United States Patent [19]

Sakagami

[11] 4,348,269

[45] Sep. 7, 1982

[54] CARRIER CONVEYING MECHANISM FOR ELECTROPHORETIC APPARATUS

[75] Inventor: Toshio Sakagami, Chofu, Japan

[73] Assignee: Olympus Optical Co., Ltd., Tokyo, Japan

[21] Appl. No.: 195,068

[22] Filed: Oct. 7, 1980

[30] Foreign Application Priority Data

Oct. 15, 1979 [JP] Japan .................... 54-141388[U]

[51] Int. Cl.³ .............................................. B01D 13/02
[52] U.S. Cl. ............................ 204/299 R; 204/180 S; 118/242; 118/239; 198/844
[58] Field of Search .......... 204/180 S, 180 G, 299 R, 204/300 R, 299 EC; 23/912; 427/2; 118/239, 242, 241; 198/842–847, 835

[56] References Cited

U.S. PATENT DOCUMENTS 1,484,248  2/1924  Austin ................................. 198/847
2,241,640  5/1941  Hemley .............................. 198/844

Primary Examiner—John D. Smith
Assistant Examiner—Bernard F. Plantz
Attorney, Agent, or Firm—Cushman, Darby & Cushman

[57] ABSTRACT

A carrier conveying mechanism for electrophoretic apparatus also serving as a support in the step of sample application comprising two wide rollers arranged on the front and rear sides respective, and a wide and thick conveying belt which is passed around said rollers and has a single or plural number of longitudinally extending grooves formed on the surface thereof, said carrier conveying mechanism being adapted in such a manner that a carrier mounted on said conveying belt is conveyed by travelling said belt with rotation of said rollers, and is made stationary by stopping the rotation of said rollers for applying a sample onto the carrier at the position located over the groove formed on the surface of said belt.

3 Claims, 3 Drawing Figures

CARRIER CONVEYING MECHANISM FOR ELECTROPHORETIC APPARATUS

BACKGROUND OF THE INVENTION (a) Field of the Invention

The present invention relates to a carrier conveying mechanism for electrophoretic apparatus which also serves as a support to be used in the step of applying samples onto said carrier.

(b) Description of the Prior Art

The electrophoresis comprises a step to apply a sample such as serum onto a carrier made of cellulose acetate or the like material, a step to electrically energize said carrier to form fractionated patters thereon, a step to color and discolor the carrier and a step of photometry. An automatic electrophoretic apparatus for carrying out these steps automatically and continuously requires a mechanism for conveying the carrier from a step to the next step. As an example of such conveying mechanism, there can be mentioned a travelling belt which conveys a carrier while mounting it on said belt. When a conveying mechanism equipped with such a belt is used with a sample applicator, operation of the conveying mechanism is stopped in the course of carrier conveyance to apply a sample onto the carrier. Speaking more concretely, operation of the conveying mechanism is stopped when the carrier reaches a predetermined position, and a sample applicator is lowered down onto the carrier and a sample is applied onto the carrier while it is mounted on the belt. In such a case, however, the sample cannot be applied adequately if the belt is kept in contact with the the carrier at the portion onto which the sample is to be applied. Further, the sample applied onto the carrier may be brought into frictional contact with the belt when the conveying mechanism is operated once again after the sample application. Therefore, the conveying mechanism uses two belts arranged at a definite interval so that they will not brought into contact with the carrier at the portions at which the sample is to be applied. In case of such a conveying mechanism, however, the carrier is flexed when the tip of the sample applicator is brought into contact with the carrier for applying a sample thereto. Such flexure is undesirable for sample applying operations. If the carrier is conveyed while it is sagged between the conveying belts, there is caused a defect that the carrier cannot be conveyed securely.

As conveying mechanisms which have corrected the above-mentioned defect, there have already known the one disclosed by Japanese published examined patent application No. 46480/78, U.S. Pat. No. 4,070,986, etc. Partial outline of this conveying mechanism is shown in FIG. 3. Speaking concretely, passed around two rollers 11 (though only one roller is shown in the drawing, two front and rear rollers are arranged) are two belts 12 and 13 on which a carrier is mounted so as to be conveyed with travelling of the belts. The reference numeral 14 represents a support arranged between the two belts and having a cavity 14a formed at the top center thereof. This support is normally placed at the position shown in the drawing and therefore causes no hindrance to conveyance of the carrier 9 with the belts 12 and 13. In case of such a conveying mechanism, the carrier 9 is conveyed as the belts 12 and 13 travels, and the conveying mechanism stops operating to make the carrier stationary when the carrier reaches the position at which a sample is to be applied thereto. At this position, a sample applicator 10 goes down and the support 14 goes up. Before the tip of the blade 10a of the sample applicator 10 is brought into contact with the carrier, however, the tip of the support 14 reaches the height of the belt, i.e., the level shown in the chain line in FIG. 3, and is stopped at this position. When the tip of the sample applicator presses the carrier 9 to apply a sample adhering to the blade 10a onto the carrier, the carrier cannot be flexed since the support is kept in contact with the bottom surface of the carrier. Further, owing to the cavity 14a formed on the top of the support 14, the portion of the carrier to which a sample is applied is not kept in contact with anything. After the sample has been applied onto the carrier, the sample applicator goes up and the support 14 goes down so that the support 14 is kept in the position shown in FIG. 3 when the conveying mechanism operates and the carrier is conveyed once again. The conventional conveying mechanism described above requires the support and, in addition, an interlocking mechanism which operates the support in conjunction with the motion of the sample applicator, thereby being very complicated in its construction. Moreover, since the top surface of the support must be in parallel with the belts when the former is raised to its upper position, the mechanism has a defect to require tedious adjustment and so on.

SUMMARY OF THE INVENTION

A general object of the present invention is to provide a carrier conveying mechanism for electrophoretic apparatus using a wide belt having longitudinally extending grooves formed on the surface thereof and serving also as a support in the step of sample application.

DETAILED DESCRIPTION OF THE PREFERRED EMBODIMENT

Figure 1:
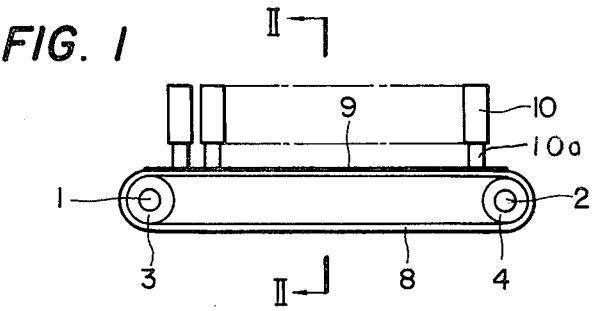
FIG. 1 shows a sectional view illustrating construction of the carrier conveying mechanism according to the present invention.
Figure 2:
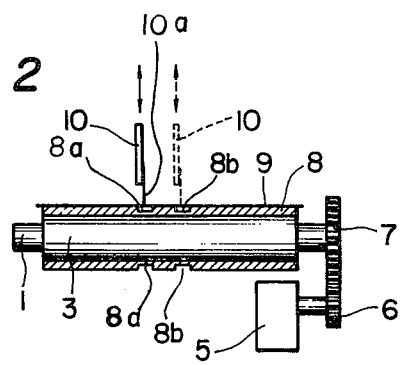
FIG. 2 shows a sectional view taken along the II—II line of FIG. 1.
Figure 3:
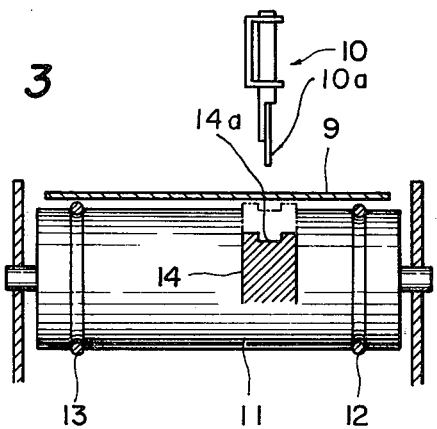
FIG. 3 shows a sectional view illustrating the construction of the conventional carrier conveying mechanism.

In FIG. 1 and FIG. 2, the reference numerals 1 and 2 represent two front and rear shafts rotatably attached to a frame (not shown), the reference numerals 3 and 4 designate wide rollers fixed to said shafts 1 and 2 respectively, and the reference numeral 5 denotes a motor which rotates the shaft 1 by way of reduction gears 6 and 7 and whose rotation and stop are controlled with an adequate controller (not shown). The reference numeral 8 represents a conveying belt which is passed around the rollers 3 and 4, said conveying belt being wide (nearly as wide as the carrier), thick and having two grooves 8a and 8b longitudinally extending continuously over the entire length of the surface of said belt. These grooves are formed at the positions corresponding to the portions of the carrier to which samples are to be applied after said carrier is placed on the belt 8. In addition, current direction may be changed in the step of electrically energizing the carrier in the electrophoretic apparatus for preventing the buffer contained in the electrophoretic apparatus from changing its pH value and other factors. When current direction is changed as described above, it is necessary to change the positions at which samples are to be applied. For this reason, the two grooves are formed on the surface of the conveying belt 8 so that either of the grooves will correspond to the positions at which samples are to be applied even when said positions are changed in accordance with current direction. Therefore, only one groove will be sufficient if current direction is not changed in the step of electrically energizing carriers. The reference numeral 9 represents a carrier placed on the conveying belt, and the reference numeral 10 designates a sample applicator.

Now the operation of the carrier conveying mechanism having the above-described construction according to the present invention will be described. First, the carrier 9 is wetted by a wetting mechanism (not shown) and therein is conveyed as it is mounted on the conveying belt 8. When the carrier 9 reaches the position at which a sample is to be applied onto the carrier, i.e., the position shown in FIG. 1, the motor 5 stops operating to make the carrier stationary. Subsequently, the sample applicator 10 is allowed to go down to apply a sample adhering to the blade 10a onto a definite portion of the carrier. In this condition, the carrier is not flexed since it is supported on the conveying belt which is wide and thick. Further, the sample is not brought into contact with the conveying belt since the groove 8a or 8b is located at the position corresponding to the sample applied. Therefore, the sample is applied precisely and not disturbed by contact with the belt or other member. After the sample has been applied, the sample applicator is raised up and the conveying mechanism is operated once again to convey the carrier to the next stage. Since the sample applied onto the carrier is always located at the position corresponding to the groove, there is no fear that the sample may be disturbed by frictional contact during the conveyance.

As is understood from the foregoing description, the carrier conveying mechanism according to the present invention does not require no particular support since it is equipped with the wide and thick conveying belt which performs conveyance of the carrier and also function of a support in the step of sample application. The carrier conveying mechanism according to the present invention requires no mechanism for moving up and down such a support, for interlocking the vertical motion of the support with that of the sample applicator, or no mechanism for controlling or driving vertical motion of the support. Therefore, the carrier conveying mechanism according to the present invention has a very simple construction. Furthermore, since the carrier conveying mechanism according to the present invention requires no support, it scarcely requires adjustment in its manufacturing stage and facilities its maintenance. Moreover, the carrier conveying mechanism according to the present invention consists of a small number of parts and can be manufactured at far lower cost.

I claim:

1. A carrier conveying mechanism for electrophoretic apparatus comprising a pair of wide rollers which are arranged on the front and rear sides respectively, of the conveying mechanism, a driving mechanism for rotating said rollers, a wide and thick conveying belt passing over said rollers, a first longitudinally extending groove formed on the surface of said conveying belt, a carrier mounted on said conveying belt and capable of being conveyed by travel of said belt upon rotation of said rollers by said driving mechanism and capable of being stopped at a predetermined position upon stopping of said driving mechanism, and a plurality of sample applicators arranged over and along said first groove and holding a sample at each tip portion thereof, each applicator being capable of applying said sample onto said carrier at a position located over said first groove when said conveying belt has stopped.

2. A carrier conveying mechanism for electrophoretic apparatus according to claim 1 wherein said conveying belt has a second longitudinally extending groove formed in parallel with said first groove on the surface thereof.

3. A carrier conveying mechanism for electrophoretic apparatus according to claim 1 wherein said conveying belt has a width substantially equal to that of the carrier.

* * * * *